US009005886B2

(12) United States Patent
Sanchez Gutierrez et al.

(10) Patent No.: US 9,005,886 B2
(45) Date of Patent: Apr. 14, 2015

(54) METHOD FOR CRYOPRESERVATION OF HUMAN SPERMATOZOA FREE FROM SEMINAL PLASMA USING A FAST AND SIMPLE ASEPTIC VITRIFICATION-DEVITRIFICATION PROCESS; PORTABLE KIT FOR CARRYING OUT THE METHOD; AND USE OF THE SAME FOR TREATMENT OF DISORDERS RELATED TO REPRODUCTIVE FAILURES

(75) Inventors: Raul Sanchez Gutierrez, Temuco (CL); Jennie Risopatron Gonzalez, Temuco (CL); Mabel Schulz Rubilar, Temuco (CL); Evgenia Isachenko, Ulm (DE); Vladimir Isachenko, Ulm (DE)

(73) Assignees: Universidad de La Frontera (CL); Universitaet Ulm (DE)

( * ) Notice: Subject to any disclaimer, the term of this patent is extended or adjusted under 35 U.S.C. 154(b) by 0 days.

(21) Appl. No.: 13/820,142

(22) PCT Filed: Feb. 16, 2011

(86) PCT No.: PCT/IB2011/050651
§ 371 (c)(1),
(2), (4) Date: Feb. 28, 2013

(87) PCT Pub. No.: WO2012/028967
PCT Pub. Date: Mar. 8, 2012

(65) Prior Publication Data
US 2013/0157250 A1   Jun. 20, 2013

(30) Foreign Application Priority Data
Aug. 30, 2010   (CL) .................................... 920-2010

(51) Int. Cl.
*A01N 1/02*   (2006.01)
(52) U.S. Cl.
CPC ............ *A01N 1/0284* (2013.01); *A01N 1/0221* (2013.01); *A01N 1/0268* (2013.01)
(58) Field of Classification Search
None
See application file for complete search history.

(56) References Cited

U.S. PATENT DOCUMENTS

2006/0046243 A1   3/2006   Stachecki et al.
2009/0081782 A1   3/2009   Yoon et al.

FOREIGN PATENT DOCUMENTS

EP       2156735 A1 *   2/2010
EP       2156735 A1 *   2/2010
WO   WO 2007/120829 A2 *  10/2007

OTHER PUBLICATIONS

Isachenko et al., Reprod. Res. 136: 167-173 (2008).*
Kundu et al., Reproduction 123: 907-913 (2002).*
Quinn et al., Ann. New York Acad. Sci. 442: 195-204 (1985).*
59th Annual Meeting of the American Society for Reproductive Medicine, "Abstracts of the Scientific Oral and Poster Sessions," Program Supplement, Oct. 12-17, 2002, *Fertility and Sterility*, vol. 76, No. 3S, Sep. 2002, p. S129.
Chen et al., "Effects of Ginsenoside Rb2 and Rc on Inferior Human Sperm Motility in Vitro," *American Journal of Chinese Medicine*, vol. 29, No. 1, pp. 155-160, 2001, Institute for Advanced Research in Asian Science and Medicine.
Critser et al., "Cryopreservation of human spermatozoa. III. The effect of cryoprotectants on motility," *Fertility and Sterility*, vol. 50, No. 2, pp. 314-320, Aug. 1988, The American Fertility Society.
Fahy et al., "Vitrification as an Approach to Cryopreservation," *Cryobiology*, vol. 21, pp. 407-426, 1984, Academic Press, Inc.
Hu et al., "Impact of three different cryoprotectants on motility of post-thaw human sperm," *Chinese Journal of Practice Medicine*, pp. 208-210, Mar. 6, 2007.
International Search Report for International Application No. PCT/IB2011/050651 mailed on Nov. 14, 2012.
Irvine Scientific, Material Safety Data Sheet for Dextran Serum Supplement, Product No. 9301, Version 2, Revised Dec. 20, 2010.
Isachenko et al., "Acrosomal status and mitochondrial activity of human spermatozoa vitrified with sucrose," *Reproduction Research*, vol. 136, pp. 167-173, 2008, Society of Reproduction and Fertility, DOI: 10.1530/REP-07-0463.
Ishachenko et al., "Cryoprotectant-Free Cryopreservation of Human Spermatozoa by Vitrification and Freezing in Vapor: Effect on Motility, DNA Integrity, and Fertilization Ability," *Biology of Reproduction*, vol. 71, pp. 1167-1173, 2004, published online before print on Jun. 2, 2004, DOI 10.1095/biolprod.104.028811.
Ishachenko et al., "Vitrification of mouse pronuclear embryos after polar body biopsy without direct contact with liquid nitrogen," *Fertility and Sterility*, vol. 84, No. 4, Oct. 2005, American Society for Reproductive Medicine, Elsevier Inc.
J. Brotherton, "Cryopreservation of Human Semen," *Archives of Andrology*, vol. 25, pp. 181-195, 1990, Hemisphere Publishing Corporation.

(Continued)

*Primary Examiner* — Patricia A Leith
*Assistant Examiner* — Erin M Bowers
(74) *Attorney, Agent, or Firm* — Merchant & Gould P.C.

(57) ABSTRACT

The present invention discloses a method for cryopreservation of human spermatozoa: the method comprises providing spermatozoa free from seminal liquid; mixing the spermatozoa with vitrification medium, wherein the main cryoprotectant agent is 0.1-0.3 M sucrose; placing the sample inside straws and rapidly freezing them; refrigerating the straws with no need of liquid $N_2$; and devitrifying the sample in a medium of the present invention. The present invention furthermore discloses a portable kit that makes easy to implement the method, said kit comprising vitrification and devitrification solutions in the volumes required to develop the method and the physical support to carry out the same, i.e. the straws. The use of this kit is also disclosed for the treatment of disorders related to reproductive failures.

7 Claims, No Drawings

(56) References Cited

OTHER PUBLICATIONS

J. Levitt, "Chryochemistry of Plant Tissue, Protein Interactions," *Cryobiology*, vol. 3, No. 3, 1966, pp. 243-251.

J. Stachecki, "Symposium: Cryopreservation and assisted human conception, an overview of oocyte cryopreservation," *Reproductive BioMedicine Online*, vol. 9, No. 2, pp. 152-163, www.rbmonline.com/Article/1192 on web Jun. 18, 2004.

Marchetti et al., "Study of mitochondrial membrane potential, reactive oxygen species, CAN fragmentation and cell viability by flow cytometry in human sperm," *Human Reproduction*, vol. 17, No. 5, pp. 1257-1265, 2002.

MP Biomedicals, LLC, Material Safety Data Sheet for Sucrose ACS Reagent Grade, Catalog No. 152584, Revised Apr. 26, 2006.

Muldrew et al., "Mechanisms of intracellular ice formation," *Biophysical Journal*, Biophysical Society, vol. 57, pp. 525-532, Mar. 1990.

Nawroth et al., "Vitrification of Human Spermatozoa Without Cryprotectants," *CryoLetters*, vol. 23, pp. 93-102, 2002.

Product Datasheet for Sucrose, http://www4.mpbio.com/ecom/docs/proddata.nsf/(webtds2)/152584.

Sanger et al., "Semen cryobanking for men with cancer—criteria change," *Fertility and Sterility*, vol. 58, No. 5, pp. 1024-1027, Nov. 1992, The American Fertility Society.

Smiley et al., "Intracellular heterogeneity in mitochondrial membrane potentials revealed by a J-aggregate-forming lipophilic cation JC-1," *Proc. Natl. Acad. Sci. USA*, vol. 88, pp. 3671-3675, May 1991, Cell Biology.

Ishachenko et al., "DNA integrity and motility of human spermatozoa after standard slow freezing versus cryoprotectant-free vitrification," *Human Reproduction*, vol. 19, No. 4, pp. 932-939, 2004, Advance Access publication Mar. 11, 2004, DOI: 10.1093/humrep/deh194.

\* cited by examiner

METHOD FOR CRYOPRESERVATION OF HUMAN SPERMATOZOA FREE FROM SEMINAL PLASMA USING A FAST AND SIMPLE ASEPTIC VITRIFICATION-DEVITRIFICATION PROCESS; PORTABLE KIT FOR CARRYING OUT THE METHOD; AND USE OF THE SAME FOR TREATMENT OF DISORDERS RELATED TO REPRODUCTIVE FAILURES

This application is a National Stage Application of PCT/IB2011/050651, filed 16 Feb. 2011, which claims benefit of Serial No. 920-2010, filed 30 Aug. 2010 in Chile and which application(s) are incorporated herein by reference. To the extent appropriate, a claim of priority is made to each of the above disclosed applications.

The invention discloses a method for cryopreservation in steps that involve vitrification and devitrification of human spermatozoa; a portable product (kit) containing the materials required to carry out this method; and its use as an aseptic, fast and simple methodology that can be used to preserve cryopreserved spermatozoa in a way that is easily implemented in laboratories with no requirement of storage in liquid $N_2$ since they can be stored at $-80°$ C. These conditions are favorable for assisted reproduction laboratories in general, since it provides a high reduction in costs in the preservation stage, mainly because of the long periods during which spermatozoa must be cryopreserved in sperm banks maintained in those laboratories.

BACKGROUND

Conventional techniques for cryopreservation of mammal cells are generally associated to disadvantages that decrease the potential use of these cells in the clinical and research fields.

Specifically, freezing spermatozoa is the most broadly used technique in assisted reproduction to preserve male gametes and provide the opportunity for future fecundation (Sanger et al., 1992). The main reported deterioration caused by cryopreservation in human spermatozoa is a marked reduction in motility (Critser et al., 1988). The primary cause of cellular damage produced during cryopreservation is caused by formation of intracellular ice crystals (Muldrew and McGann, 1990). This cellular damage involves the irreversible breakage of the plasmatic and nuclear membranes with a subsequent alteration of cellular organelles (Brotherton, 1990).

Traditional spermatozoa freezing methods use intracellular cryoprotectants because they have the ability to permeate the plasmatic membrane and are able to penetrate the cell. The efficiency associated to sperm function using this type of cryoprotectants is low, with at most 45% of conservation of at least one relevant cell function that is important for this type of cells, such as motility, because permeable cryoprotectants are cryotoxic and exert damage to intracellular organelles and the plasmatic membrane, notably decreasing the fecundation capacity of spermatozoa. Furthermore, this technique has a high cost due to the type of media used and the prolonged preservation in liquid $N_2$, and therefore its use is limited to higher income populations or to programs with costs that are not covered by the health system, as in developed countries.

Vitrification is an extremely fast cryopreservation method that requires less execution time, is safer and has a lower effective cost than traditional freezing. Vitrification has been widely investigated for embryos and oocytes (Chen et al., 2001; Isachenko et al., 2005), but is much undeveloped for spermatozoa, and few publications about this topic can be found (Isachenko et al., 2004; Isachenko et al., 2008). In these last publications, the authors, who are also the inventors of the present invention, developed the basis for a cryopreservation method for spermatozoa, free from toxic cryopreservants. However, this methodology is not aseptic and does not have the characteristics of portability, simplicity and efficacy, which are indeed provided by the kit and optimal composition of the media of the present invention.

This method is similar to glass formation, which is an intrinsic property of all liquids that only needs a sufficiently fast freezing rate to avoid the passage through the crystalline stage. For this reason, vitrification does not cause protein molecules to approach to each other as in traditional freezing (Levitt, 1966), which avoids formation of disulfide bridges that cause protein denaturation (Fahy et al., 1984).

Vitrification is carried out in small volumes in such a way as to immerse the sample directly in liquid nitrogen to increase the cooling rate and decrease ice crystal formation (Nawroth et al., 2002). This contributes even more to facilitate the methodology and costs of spermatozoa vitrification, since it does not require special cryobiological equipment. Likewise, it allows adequate preservation of sperm motility, but the most significative advance of this technique is that it does not damage sperm DNA.

The Patent Application US20080026361, filed in 2007, discloses a composition comprising a cryoprotectant, a protective membrane that stabilizes or assists in stabilizing spermatozoal membranes and a radical scavenger, wherein the cryprotectant is a sugar, such as sacarose, the protective membrane can be a protein agent or a non-protein agent or a combination of the same, albumin being an example of a possible protein agent, and the radical scavenger can be a reducing agent or an antioxidant. This application claims a kit that comprises a vitrification composition, an insulating container, a cryogenic pack, a receptacle for spermatozoa, such as straws, glass ampoules, cryotubes or cryovials. However, the application uses a cryoprotectant solution with a different composition to that of the present invention; using a medium mainly containing glycerol (TYB) and optionally supplemented with monothioglycerol.

The Patent Application US20090305224 (family of WO2007120829), filed on 2009, describes a method for cryopreservation of mammal cells such as oocites, hepatocytes, stem cells, embryos or cygotes, useful as a clinical or research tool (e.g. in reproductive technology, cell transplant, tissue engineering or regenerative medicine). The application focuses on the determination of the thermal performance parameters of different materials and solutions, such as thermal conductivity of diverse materials, mainly quartz. Moreover, this patent application does not exemplify the use of the proposed method for specific vitrification of human spermatozoa and does not exemplify the straw materials of the present invention, since the use of quartz not only increases the associated costs, but also restricts the portability and applicability of thermal conductors of this material in a commercial kit.

The article "Impact of three different cryoprotectants on the motility of post-thaw human sperm" (Hu et al., 2007) is aimed at comparing the effect levels of a glucose cryoprotectant or cryoprotectants with different sucrose concentrations on the motiliy of human spermatozoa after thawing. In the study, no large differences with other cryoprotectants were observed when using glucose as a cryoprotectant at a concentration of 0.1 M. However, when using sucrose at a concentration of 0.2 M, a significant decrease in spermatozoal damage was observed in comparison with other cryoprotectants. Surprisingly, using of a sucrose concentration in the range higher than 0.2 M constitute an optimal concentration for the spermatozoa vitrification medium of the method of the present invention.

The article "Acrosomal status and mitochondrial activity of human spermatozoa vitrified with sucrose" (Isachencko et al., 2008) investigates the capacity of sucrose as a cryoprotectant for spermatozoa against mitochondrial damage, and its effect on cryocapacitation and acrosomal reaction during vitrification. The procedure includes the selection of spermatozoa using different culture media, where one particular medium comprises HTF (Human Tubal Fluid) supplemented with 0.25 M sucrose and 1% HSA (Human Serum Albumin). After vitrification, different spermatozoal functional properties were evaluated, and the article concludes that the medium with sucrose was significantly better to preserve spermatozoal progressive motility after devitrification. The methodology that has been used to vitrify the cell suspension consisted in vitrifying 30 μL spheres that were dropped directly into liquid nitrogen, this being an effective but not aseptic methodology, since droplets directly contacted the liquid nitrogen. Surprisingly, the use of the method of the present invention, besides being aseptic, allows the preservation of a volume up to 100 μL, and thus is a more efficient method when larger sample volumes are available.

SUMMARY

The techniques used for freezing spermatozoa require a specific equipment and liquid nitrogen to keep the samples for some time, which implies high costs. Therefore, the access to this preservation alternative is limited to a small group of patients that can afford the procedure. The conventional freezing technique has a low recovery ratio of motile and functional spermatozoa, since the entire seminal fluid sample (spermatozoa+seminal plasma) is frozen together with all biological contaminants that could be present therein (bacteria, fungi and viruses).

The present invention solves the technical problem by optimizing the use of materials and time involved in cryopreservation by vitrification, allowing best results to be obtained using a suspension of vitrified spermatozoa in 0.25 M sucrose, with a high percentage of motile, viable spermatozoa having an acrosomal integrity higher than 80% after devitrification. The use of sucrose instead of other cryopreservants avoids osmotic damage and crystallization. Yet more importantly, spermatozoa that were vitrified in sucrose conserved a better sperm function, since more than 60% presented an unaltered mitochondrial membrane potential ($\Delta\psi$MMit). The measuring parameter $\Delta\psi$MMit is the most sensible way to evaluate spermatozoal function (Marchetti et al., 2002).

The cryopreservation technique of the present invention implies vitrifying only motile spermatozoa selected using sperm selection techniques, in such a way as to remove abnormal or damaged spermatozoa and infiltrated cells, as well as all the seminal plasma.

Moreover, it protects the reproductive capacity, cryopreserving sperm function in a highly effective way using a vitrification kit for human spermatozoa with a formulation with no permeable cryoprotectans that is able to protect the integrity and reproductive function with no special storage equipment requirements. It will also be possible to implement an easily applicable vitrification technique for spermatozoa using a vitrification kit with a cost at least 50% lower than the cost of a traditional freezing kit for a demanding market in developed countries that currently uses the conventional freezing method. Likewise, this low cost will allow the use and distribution to developing countries.

DETAILED DESCRIPTION

This invention discloses a method for cryopreservation of spermatozoa using vitrification and devitrification of human spermatozoa, comprising the following steps:

(a) providing spermatozoa free from seminal plasma, using some of the known techniques for spermatozoa selection, such as migration by sedimentation, "swim up" or centrifugation in a discontinuous density gradient, to separate spermatozoa from the seminal liquid, because the removal of seminal fluid in this stage maintains asepsis in the sample and prevents the presence of contaminating microorganisms in the sample that could be present in the seminal liquid;

(b) resuspending and mixing the spermatozoa in a 1:1 volumetric ratio with a vitrification medium comprising:
  i) a spermatozoal buffer medium, such as e.g. Gamete (COOK®) buffer or Human Tubal Fluid (HTF, Isanchenko et al., 2008) medium,
  ii) a non permeating cryoprotectant such as sucrose, with a final concentration between 0.15 and 0.30 M during the vitrification process, preferably selecting a final concentration of 0.25 M sucrose in the medium, and
  iii) a dextran supplemented serum, such as e.g. Dextran SERUM Supplement (IrvineScientific®) or a human serum albumin supplemented serum;

(c) mixing and adjusting the final concentration of spermatozoa within a range from $0.2\times10^6$ to $1.8\times10^6$ spermatozoa per 100 μl of the vitrification medium previously cited in step (b); preferably adjusting the final concentration within a range from $0.5\times10^6$ to $1.8\times10^6$ spermatozoa per 100 μl of medium, using a rule of three simple to calculate the volume of the dilution;

(d) immediately depositing 100 μl of the suspension of spermatozoa in vitrification medium obtained in step (c) in a thermoconductor receptacle made from a thermoconductor material, such as e.g. plastic; the vitrification receptacle comprising a system of two plastic straws horizontally placed in such a way as to leave 1 cm with no liquid at the ends of the first straw; a 0.25 ml straw being placed inside a second 0.5 ml straw that is subsequently sealed at the ends. The two-straw system containing 0.5 ml and 0.25 ml straws without a transparent wick (Minitub) sealed with the sperm inside keeps the asepsis of the sample achieved in step (a);

(e) immersing the sealed straws containing the sperm in liquid $N_2$, keeping them in horizontal position, wherein sample vitrification is preferably carried out by maintaining the straws in the liquid $N_2$ for no more than 5 seconds;

(f) keeping the straws at a temperature lower than −75° C. after vitrifying the sperm suspension; the storage of spermatozoa having place at a temperature between −75° C. and −85° C. in a freezer, with no requirement of liquid $N_2$ to store and preserve the samples in the straws;

(g) devitrifying the sample by introducing the 0.25 ml straw containing the vitrified sample in a devitrification medium comprising:
  i) spermatozoal buffer medium such as the buffer medium used in step (b), part (i),
  ii) 1% weigth/volume HTF-BSA, wherein HTF (Human Tubal Fluid) is commercially available from e.g. Irvine, and BSA is commercially available from e.g. Sigma, with 96-99% bovine albumin content, and iii) a dextran supplemented serum such as e.g. the serum used in step (b), part (iii);

wherein devitrification is carried out first by placing the samples to be devitrified in a container with liquid $N_2$ and then introducing three (3) 0.25 ml straws with sample in a tube with 5 ml of devitrification medium incubated at a temperature ranging from 36.5 to 37.5° C. in a heating block.

Alternatively, an additional step can be carried out, comprising: centrifugating the sample at 1,800 rpm for 5 minutes to remove the devitrification medium; subsequently resuspending the supernatant-free sample in spermatozoal medium and evaluating spermatozoal motility; and using the desired reproduction technique.

The present invention provides a kit containing enough medium for 50 straws; a volume of vitrification medium (at least 5 ml) and a volume of devitrification medium (at least 100 ml) to devitrify 50 samples; fifty (50) 0.5 straws, fifty (50) 0.25 ml straws, and instructive and support materials for implementation of the method. The use of this kit stands out for the treatment of disorders related to reproductive failures or in patients that are undergoing an assisted reproduction treatment, and also in patients that require the preservation of their fecundation capacity in certain pathologies such as cancer or viral infections such as VIH that threaten their reproductive capacity.

EXAMPLES

Aseptic Vitrification of Spermatozoa

Seminal liquid samples were obtained from patients in a sexual abstinence period of at least 48 hours before sample collection, with previous signature of an informed consentment. All samples contained at least 20,000,000 spermatozoa per ml; 50% thereof having progressive motility and normal morphology in ≥5%.

Normozoospermic seminal liquid samples were selected using the "swim up" technique. This technique allows obtaining spermatozoal fractions with the highest levels of activity and viability.

Spermatozoa were resuspended in Vitrisperm Medium, prepared from 0.495 ml of Gamete Buffer Medium (COOK®), 0.495 ml of a 0.5 M sucrose solution (MP Biomedicals, Cat. 152584), and 0.010 ml of a dextran supplemented serum (IrvineScientific, Cat. 9301).

Selected spermatozoa were mixed with vitrification medium (in a 1:1 volumetric ratio) just prior to the vitrification process, since it is not advisable to subject the cells to the vitrification medium for too much time, and the final concentration was adjusted to $0.5 \times 10^6$-$1.8 \times 10^6$ spermatozoa per 100 μl of vitrification medium. Subsequently, with the aid of a pipetting device 100 μl of suspension were placed in each 0.25 ml straw, leaving a 1-cm space at each end.

Subsequently, the 0.25 ml straw was horizontally inserted inside the 0.5 ml straw and the open ends of the 0.5 ml straw were sealed. It is important to always keep the horizontal position of the straw, from the filling stage to their immersion in liquid $N_2$.

Aseptic Devitrification of Spermatozoa

A container was filled with liquid $N_2$ and straws to be devitrified were put inside. Simultaneously, 5 ml of devitrification medium, containing 4.95 ml of Gamete Buffer (COOK®) and 0.05 ml of dextran supplemented serum (IrvineScientific, Cat. 9301), were equilibrated at 37° C.

A heating block (water bath) was placed close to the container at 37° C. with the tubes with 5 ml of devitrification medium. 1 tube with 5 ml of medium was used for each 3 straws.

Using tweezers, the straws were recovered one by one from the liquid $N_2$, the 0.5 ml straw was cut in the place with a marked end, and the 0.25 ml straw was dropped by inverting the previously cut 0.5 ml straw into devitrification medium, aiding the process by moving the straw with the help of sterile tweezers. The 0.25 ml straw was stabilized in the medium for at least 5 minutes with incubation at 37° C. The medium was centrifuged at 1,800 rpm for 5 minutes to concentrate and remove the supernatant. The pellet was washed once with spermatozoal medium (Gamete Buffer) and then a selection technique was applied, or assays were immediately performed to evaluate the status of the spermatozoa after vitrification.

Evaluation of Sperm Quality

Diverse sperm quality parameters were contrasted, mainly sperm motility and viability, for conditions of: a non-cryopreserved control sample, the sample subjected to the vitrification/devitrification process as taught in the former examples; and a sample frozen/thawed in liquid $N_2$ with a commercial cryoprotectant (traditional freezing method). All the assays described in the following section were performed using a FACSCalibur flow cytometer (Beckton Dickinson).

Motility was measured using a Makler chamber. Motility was estimated using light microscopy with 400× magnification. This parameter was measured only for spermatozoa having a progressive motility in categories a and b (a, fast linear progression; b, slow linear progression).

The acrosomal membrane integrity was determined using the PSA-FITC Sigma L-2857 commercial kit. Sperm cryocapacitation was determined measuring the translocation of phosphatidyl-serine, using the ANNEXIN V-FITC APOPTEST™-FITC commercial kit (Nexins Research).

Furthermore, the mitochondrial membrane potential (ΔψMMit) was measured using a single cationic dye known as JC-1 (Smiley et al., 1991). The assay was carried out according to the conditions of a commercial kit for detection of mitochondrial membrane permeability (Kit AK-116, Mit-E-ψ), BIOMOL International LP).

The results obtained for these four assays are presented in percentage terms in the following summarizing table.

| Assay | Result % | Sample condition | | |
|---|---|---|---|---|
| | | Control | Vitrification | Freezing |
| Translocation of phosphatidyl-serine | mean | 1.555 | 1.59 | 20.05 |
| | standard deviation | 1.027 | 0.9317 | 1.06 |
| Loss of membrane integrity | mean | 3.43 | 28.03 | 41.43 |
| | standard deviation | 3.459 | 6.919 | 1.688 |
| Mitochondrial membrane potential | mean | 89.3 | 71.65 | 29.45 |
| | standard deviation | 10.49 | 1.708 | 4.342 |
| Motility | mean | 95.78 | 77.72 | 28.32 |
| | standard deviation | 1.704 | 2.26 | 3.408 |

From the former table, the surprising results of the method used in the present invention stand out with respect to the freezing technique that is commonly used in laboratories. In these results, phosphatidyl-serine translocation indicates a behavior that is very similar to that of a fresh non-vitrified sample. The loss of integrity of the acrosomal membrane is lower than that obtained with the freezing methodology, wherein the ΔψMMit value of the vitrified/devitrified sample is very similar to the corresponding value of the control sample. It can be also observed that the loss of motility of the vitrified sample is much lower than that of the frozen sample.

What is claimed is:

1. A method for cryopreservation of human spermatozoa free from seminal plasma using an aseptic vitrification-devitrification process, wherein said method comprises:
    (a) providing spermatozoa free from seminal liquid;
    (b) resuspending and mixing the spermatozoa obtained in step (a) in a 1:1 volumetric ratio with a vitrification medium comprising:
        i) a buffering medium for spermatozoa,
        ii) a non-permeable cryoprotectant, and
        iii) a dextran supplemented serum;
    (c) mixing and adjusting the final concentration of spermatozoa within a range from $0.2 \times 10^6$ to $1.8 \times 10^6$ spermatozoa per 100 µl of vitrification medium;
    (d) placing 100 µl of the mixture of spermatozoa and vitrification medium immediately after step (c) in a 0.25 mL straw, then placing this straw inside a 0.5 mL straw having an open end;
    (e) immersing the 0.5 ml straw with the sperm content in horizontal position in liquid $N_2$ for no more than 5 seconds;
    (f) keeping the sperm sample inside the straws at a temperature lower than −75° C;
    (g) devitrifying the sample by introducing the straw containing the sperm sample in a devitrification medium comprising:
        i) the buffering medium for spermatozoa,
        ii) HTF supplemented with 1% w/v BSA, and
        iii) a substituting serum supplemented with dextran, incubated at a temperature ranging from 36.5 to 37.5° C.

2. The method for cryopreservation of spermatozoa according to claim 1, wherein the non-permeable cryoprotectant comprises sucrose at a final concentration ranging from 0.15 to 0.30 M.

3. The method for cryopreservation of spermatozoa according to claim 1, wherein the final spermatozoa amount in step (c) is adjusted in a range from $0.5 \times 10^6$ to $1.8 \times 10^6$ spermatozoa per 100 µL of vitrification medium.

4. The method for cryopreservation of spermatozoa according to claim 1, wherein during step (d) the straws are plastic, and wherein, after placing the 0.25 mL straw containing the spermatozoa sample inside the 0.5 mL straw, the 0.5 mL straw is sealed at its open end.

5. The method for cryopreservation of spermatozoa according to claim 1, wherein, in step (e), the straws are immersed in liquid $N_2$ for 5 seconds.

6. The method for cryopreservation of spermatozoa according to claim 1, wherein said storage of spermatozoa in step (f) takes place at a temperature between −75 to −85° C. in a freezer, avoiding the use of liquid $N_2$.

7. The method for cryopreservation of spermatozoa according to claim 1, wherein the vitrification medium does not contain a permeable cryoprotectant.

* * * * *